United States Patent
Allen et al.

(10) Patent No.: US 6,287,452 B1
(45) Date of Patent: *Sep. 11, 2001

(54) ELECTRODE FOR THE ELECTROCHEMICAL DETECTION OF NITRIC OXIDE

(75) Inventors: Barry W. Allen, Durham, NC (US); Louis A. Coury, Jr., Lafayette, IN (US); Claude A. Piantadosi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,371

(22) Filed: Sep. 20, 1999

Related U.S. Application Data

(63) Continuation of application No. 08/942,354, filed on Oct. 1, 1997, now Pat. No. 5,980,705.
(60) Provisional application No. 60/027,355, filed on Oct. 2, 1996.

(51) Int. Cl.$^7$ ..................................................... G01N 27/26
(52) U.S. Cl. ...................... 205/777.5; 205/781; 205/792; 205/793; 204/403; 204/415; 204/291; 422/82.03; 600/309; 600/345; 600/353
(58) Field of Search .................................... 204/403, 415, 204/291; 205/777.5, 778, 781, 792, 793; 600/309, 345, 353

(56) References Cited

U.S. PATENT DOCUMENTS

| | | |
|---|---|---|
| 4,158,044 | 6/1979 | Takabatake et al. . |
| 4,913,780 | 4/1990 | Habermann et al. . |
| 5,358,889 | 10/1994 | Emesh et al. . |
| 5,409,591 | 4/1995 | Baker et al. . |
| 5,466,350 | 11/1995 | Baker et al. . |
| 5,565,075 | 10/1996 | Davis et al. . |
| 5,980,705 | * 11/1999 | Allen et al. ........................ 204/291 |

FOREIGN PATENT DOCUMENTS

| | | |
|---|---|---|
| WO 93/215/18 | 10/1993 | (EP) . |
| WO 94/02845 | 2/1994 | (EP) . |
| WO 96/16593 | 6/1996 | (EP) . |

OTHER PUBLICATIONS

The Chemistry of the Rarer Platinum Metals (Os, Ru, Lr and Rh), W.P. Griffith, Imperial College, London, 1967 Interscience Publishers, a division of John Wiley & Sons, London, New York, Sydney No month available.

Chemically modified electrode for the selective and sensitive determination of nitric oxide (NO) in vitro and in biological systems, F. Pariente, J.L. Also, H.D. Abruna, Department of Chemistry, Baker Laboratory, Cornell University, Ithaca, NY 14853–1301, USA, Received Dec. 21, 1993; in revised form Apr. 25, 1994.

Preliminary note; The use of gold electrodes in the electrochemical detection of nitric oxide in aqueous solution; Fethi Bedioui, Stephane Trevin and Jacques Devynck; Laboratoire d'Electrochimie det de Chimie Analytique (URA n° 216 due CNRS), Ecole Nationale Superieure de Chijie de Paris, 11 rue Pierre et Marie Curie 75231, Paris Cedex 05 (France); (Received May 31 1994; in revised form Jun. 24, 1994).

Technical Note; An electrochemical microprobe for detecting nitric oxide release in brain tissue; Katsuei Shibuki; Laboratory for Neural Networks, Frontier Research Program, RIKEN, Wako, (Japan) (Received May 22, 1990; Accepted Jun. 4, 1990).

Practical nitric oxide measurement employing a nitric oxide–selective electrode; K. Ichimori, H. Ishida, M. Fukahori, and E. Murakami; Department of Physiology 2, Tokai University, School of Medicine, Bohseidai, Ishara, Kanagawa 259–11, Japan No month/year available.

Nitric Oxide Measurement by Electromechanical Methods; Tadeusz Malinski, Oakland University, Rochester, Michigan, USA; Leszek Czuchajowski; University of Idaho, Moscow, Idaho, USA No month/year available.

Metal Nitrosyls; George B. Richter–Addo; Peter Legzdins; Department of Chemistry; The University of British Columbia; Vancouver, Canada; New York Oxford Press 1992 No month available.

Encyclopedia of Electrochemistry of the Elements; Editor—Allen J. Bard; Department of Chemistry; University of Texas, Austin, Texas; vol. VI; Marcel Dekker, Inc., New York and Basel No month/year available.

Electrochemical Methods Fundamentals and Applications; Allen J. Bard, Department of Chemistry, University of Texas; Larry R. Faulkner, Department of Chemistry, University of Illinois No month/year available.

Spectroscopic and Electrochemical Response to Nitrogen Monoxide of a Cationic Iron Porphyrin Immoblized in Nafion–coated Electrodes or Membranes; Joseph Hayon, Dan Ozer, Judith Rishpon and Armand Bettelheim; Nuclear Research Centre, PO Box 9001, Beer–Sheva 84190, Israel; Department of Biotechnology, Tel–aviv University, Ramat Aviv 69978, Isarael No month/year available.

(List continued on next page.)

Primary Examiner—Bruce F. Bell
(74) Attorney, Agent, or Firm—Nixon & Vanderhye P.C.

(57) ABSTRACT

Nitric oxide-specific electrodes are useful for in situ detection of nitric oxide in biomedical applications and have at least a surface region thereof which is capable of forming complexes with nitric oxide, for example, nitrosyl complexes. The nitric oxide complexes formed at the surface of the electrodes apparently increase the concentration of nitric oxide available for detection, thereby leading to significantly improved relative responses as compared to other known nitric oxide electrode materials. Most preferably, the electrode has at least an exterior surface region which contains ruthenium and/or at least one oxide of ruthenium. The electrodes are advantageously conditioned in saline solution at +675 mV for about two hours.

17 Claims, 3 Drawing Sheets

OTHER PUBLICATIONS

Incorporation of Anionic Metalloprorphyrins Into Poly(Pyrrole–Alkylammonium) Films—Part 2. Characterization of the Reactivity of The Iron(III) Porphyrininc–Based Polymer; Fethi Bedioui, Yves Bouhier, Christian Sorel, Jacaques Devynck, Liliane Coche–Guerente, Alain Deronzier and Jean Claude Moutet; Laboratoire d'Electrochimie Analytique et Appliquée (U.R.A. No. 216 du C.N.R.S.), Ecole National Supérieure de chimie de Paris, 11 Rue Pierre et Marie Curie, 75231 Paris Cedex 05, France Laboratoire d'Electrochimie Organique et de Photochimie Rédox (U.R.A. No. 1210 du C.N.R.S.), Univeersité Joseph Fourier, BP 53X, 38041 Grenoble Cedex, France (Received May 17, 1993; in revised from Jun. 16, 1993).

A Discussion of Electrochemical Techniques for the Detection of Nitric Oxide; David A. Wink, Danae Christodoulou, May Ho, Murali C. Krishna, John A. Cook, Harold Haut, J. Kemp Randolph, Melani Sullivan, George Coia, Royce Murray, and Thomas Meyer; Chemistry Section, Laboratory of Comparative Carcinogenesis, National Cancer Institute, Frederick Cancer Research and Development Center, Frederick, Maryland 21702; Radiation Biology Section, Radiation Biology Branch, National Cancer Institute, Bethesda, Maryland 20892; Medical Systems, Inc., One Plaza Road, Greenvale,New York 11548; and Department of Chemistry, University of North Carolina, Chapel Hill, North Carolina 27514 No month/year available.

The Role of Nickel as Central Metal in Conductive Polymeric Porphyrin Film for Electrocatalytic Oxidation of Nitric Oxide; Aleksander Ciszewski, Eugeniusz Kubaszweski and Marek Loźyński; Institute of Chemistry and Applied Electrochemistry, Poznań University of Technology, PL–60–965 Paznań , Poland; Received Apr. 10, 1995; Final version: Jun. 1, 1995.

Electrochemical and spectrophotometric study of the behavior of electropolymerized nickel porphyrin films in the determination of nitric oxide in solution; Stéphane Trevin, Fethi Bedioui, Jacques Devynck; Laboratoire d'Electrochimie et Chimie Analytique (URA No. 216 due CNRS), Ecole Nationale Superirure de chimie de Paris, 11 rue Pierre et Marie Curie, 75231 Paris Cedex 05. France; Received Mar. 29, 1995; revised Sep. 11, 1995; accepted Sep. 14, 1995.

Methods in Nitric Oxide Research; Edited by Martin Feelisch; Schwarz, Schwarz Pharma AG, Monheim, Germany and Jonathan S. Stamler, Duke University Medical Center, North Carolina, USA No month/year available.

Metal Nitrosyls; George B Richter–Addo; Peter Legzdins; Department of Chemistry; The University of Bristish Columbia, Vancouver, Canada; Oxford University Press, 1992 No month available.

Vadimsky et al, "Ru and $RuO_2$ as Electrical Contact Materials: Preparation and Environmental Interactions", *J. Electrochem. Soc.*: Solid–State Science and Technology, pp. 2017–2023 (Nov. 1979).

* cited by examiner

ELECTRODE FOR THE ELECTROCHEMICAL DETECTION OF NITRIC OXIDE

CROSS-REFERENCE TO RELATED APPLICATION

This application is a continuation of U.S. Application Ser. No. 08/942,354 filed on Oct. 1, 1997 (now U.S. Pat. No. 5,980,705), and is based on, and claims domestic priority benefits under 35 USC §119(e) from, U.S. Provisional Application Ser. No. 60/027,355 filed on Oct. 2, 1996, the entire content of each application being expressly incorporated hereinto by reference.

GOVERNMENT GRANT STATEMENT

This invention was made with Government support under Grant No. 2 PO1 HL42444-06 awarded by the National Institutes of Health. The Government has certain rights in the invention.

FIELD OF THE INVENTION

The present invention generally relates to the field of electrochemical detection of nitric oxide. In preferred embodiments, the present invention relates to electrodes and microelectrodes having improved responses to nitric oxide by chemically increasing the concentration of nitric oxide available for detection at the electrode surface and/or catalyzing the electrolysis of nitric oxide.

BACKGROUND OF THE INVENTION

Nitric oxide has just recently been identified as a molecule which plays a fundamental role in biological processes. As a result, research into the physiology and pathology of nitric oxide has grown explosively. This research activity has, in turn, created a demand for accurate and precise techniques for the determination of nitric oxide (NO.), a free radical gas that is short-lived in biological materials.

Several methods for detecting nitric oxide in biology and medicine are well established. These include spectrophotometry, chemiluminescence, and paramagnetic resonance. These are ex situ techniques, however. That is, a sample of biological fluid, for example the extracellular fluid in a tissue or the support buffer in a suspension of cells, must be analyzed out of its biological context. The measurements made on such samples reflect nitric oxide concentration at a single time, and when assembled in a series make a discontinuous record. Therefore, these methods, though valuable, are not ideal for following rapid processes, because changes in nitric oxide concentration are not observed if they occur between sampling points. However, the ability to follow rapid changes is important because nitric oxide is unstable in the presence of oxygen, persisting but a few minutes or seconds in biological systems.

Recently, electrodes for the direct electrochemical detection of nitric oxide have been developed. The earliest of these electrodes, known colloquially as the "Shibuki electrode", is a modification of an electrode for detecting $O_2$ and functions to exclude interfering species by means of a membrane permeable only to gases. See, K. Shibuki, Neuroscience Research, 9 (1990) 69–76 (the entire content of which is expressly incorporated hereinto by reference). The Shibuki electrode uses a Pt electrode to oxidize nitric oxide at 800 mV and to register the resulting oxidation current. This sensor is reported to have limited biological usefulness, because it does not respond linearly to nitric oxide concentrations greater than 1 $\mu$M and is subject to a destructive buildup of the oxidation products of nitric oxide within the enclosed electrolyte surrounding the Pt electrode.

More recently, another method became available, using a metalloporphyrin membrane electrochemically deposited on a carbon fiber electrode. See, T. Malinski et al, Nature, vol. 358, 676–677 (1992); T. Malinski et al, "Nitric Oxide Measurement by Electrochemical Methods", Methods in Nitric Oxide Research, chapter 22 (1996); and Published International Patent Application No. WO 93/21518 to T. Malinski (the entire content of each publication being expressly incorporated hereinto by reference). This sensor is constructed by electrochemically depositing a metalloporphyrin, for example nickel-tetrakis (3-methoxy-4hydroxyphenyl) porphyrin, on a carbon electrode (which may be as small as a single carbon fiber a few $\mu$m in diameter, or less). The porphyrin surface is then coated with a final layer of Nafion™ (Dupont), a fluorocarbon polymer that forms a network of interconnected cavities lined with sulfonate groups ($SO_3^-$). Cations and neutral solutes are conducted through the cavities with the anions being excluded. Direct measurements of nitric oxide have been reported using this porphyrinized electrode, with good sensitivity and selectivity. Furthermore, this porphyrinized electrode can be produced in micron or submicron tip diameters, suitable for extra- and intra-cellular measurements. Its disadvantages include the difficulty of handling micron-diameter carbon fibers, which require manipulation under a microscope with cold illumination (or under water) to eliminate thermal convection currents that disturb the fibers. Furthermore, the fibers, though strong for their size, are easily broken and are not degraded or absorbed in biological tissue. There are additional concerns about the exact chemical mechanism by which this electrode detects nitric oxide, since carbon fibers without a porphyrin coating or with a coating of porphyrin without a metal ligand can also detect nitric oxide with significant sensitivity.

A biochemically-modified electrode has also been proposed that employs Cytochrome c as a nitric oxide sensor, catalyzing the electrochemical reduction of nitric oxide and $NO_2^-$ at –580 mV. See, K. Miki et al, Journal of Electroanalytical Chemistry, 6, 703–705 (1993) (the entire content of which is expressly incorporated hereinto by reference).

Nitric oxide-detecting electrodes have also been constructed with wires of precious metals, notably platinum and gold. See, F. Pariente et al, "Chemically modified electrode for the selective and sensitive determination of nitric oxide (NO) in vitro and in biological systems", Journal of Electroanalytical Chemistry, 379, 191–197 (1994) and F. Bedioui et al, "The use of gold electrodes in the electrochemical detection of nitric oxide in aqueous solution", Journal of Electroanalytical Chemistry, 377, 295–298 (1994) (the entire content of each publication being hereby expressly incorporated hereinto by reference). Furthermore, a porphyrinic-based platinum-iridium electrode has also been constructed and is available commercially. See, K. Ichimori et al, "Practical nitric oxide measurement employing a nitric oxide-selective electrode", Ref. Sci. Instrum., 65 (8) August 1994 and H. Miyoshi, FEBS Letters, 345, 47–49 (1994) (the entire content of each publication being hereby expressly incorporated hereinto by reference).

Thus, although there have been prior proposals in the literature, the development of electrodes for the electrochemical detection of nitric oxide has yet to reach the level that would allow widespread use in biomedical research. Such an electrode must be: (1) highly sensitive (with limits of detection for nitric oxide in the nanomolar range and below); (2) highly selective for nitric oxide against interfering anions; (3) easy to prepare reproducibly in very small diameters (10 μm or less); (4) able to respond rapidly to nitric oxide, whose half-life is but a few seconds in physiological conditions; and (5) stable for minutes to hours in biological fluids and tissues. It is towards fulfilling such needs that the present invention is directed.

SUMMARY OF THE INVENTION

Broadly, the present invention relates to electrodes which exhibit an increase in electrical current due to the electrolysis of nitric oxide either by increasing the concentration of nitric oxide available at the electrode surface or by increasing the rate constant of the electrolysis at a given potential. More specifically, the electrodes of this invention have a surface region prepared from a material (for example, the element ruthenium) which is known to be capable of forming complexes with nitric oxide when exposed to nitric oxide. Such complexes may include nitrosyl complexes, M—NO (where M is a metal), isonitrosyl complexes, M—ON, nitrosyl-isonitrosyl complexes, M—NO—M' (where M' is metal that may or may not be the same as M), and NO complexes involving both metals and non-metals (including, but not limited to metal-nitrosyl-chloro complexes, such as ruthenium-nitrosyl-chloro complexes), and any other complexes involving one or more molecules of NO (in any of its oxidation states) with one or more other atoms or molecules. It is presently believed that the formation of such nitrosyl complexes will increase the selectivity of an electrode to nitric oxide over other substances because of the specificity of the process by which nitrosyl complexes are formed. In addition, the present invention offers the possibility of indirect detection of nitric oxide, since under certain conditions the formation of complexes with nitric oxide on the electrode surface may inhibit the electrolysis of other electroactive species (e.g., chloride, Cl$^-$), thereby causing a detectable change in background current. This change in background current may be significantly larger than the current due to direct oxidation or reduction of nitric oxide.

Most preferably, the electrodes of this invention include ruthenium, which in and of itself is an element known to form the greatest number of distinct nitrosyl complexes. (See, Griffith, The Chemistry of The Rarer Platinum Metals, Interscience Publishers, pp. 174–175 (1967), the entire content of which is expressly incorporated hereinto by reference.) The electrodes of this invention may thus be prepared from ruthenium, or have a coating prepared from ruthenium on a core of supporting material. Alternatively, the ruthenium may be combined with one or more metals or non-metals as may be desired.

Included within the scope of this invention are other materials that may be devised which also enhance the electrolysis of nitric oxide by means of a significant ability to form complexes with nitric oxide. Such materials include metals, their inorganic compounds, and organic compounds, including but not limited to elements and compounds described in G.B. Richter-Addo et al, Metal Nitrosyls, Oxford University Press (1992), the entire content of which is expressly incorporated hereinto by reference. Examples include, but are not limited to, Ti, Co, W, and other transition metals.

BRIEF DESCRIPTION OF THE ACCOMPANYING DRAWINGS

Reference will hereinafter be made to the accompanying drawing FIGURES, wherein.

DETAILED DESCRIPTION OF THE INVENTION

Figure 1:
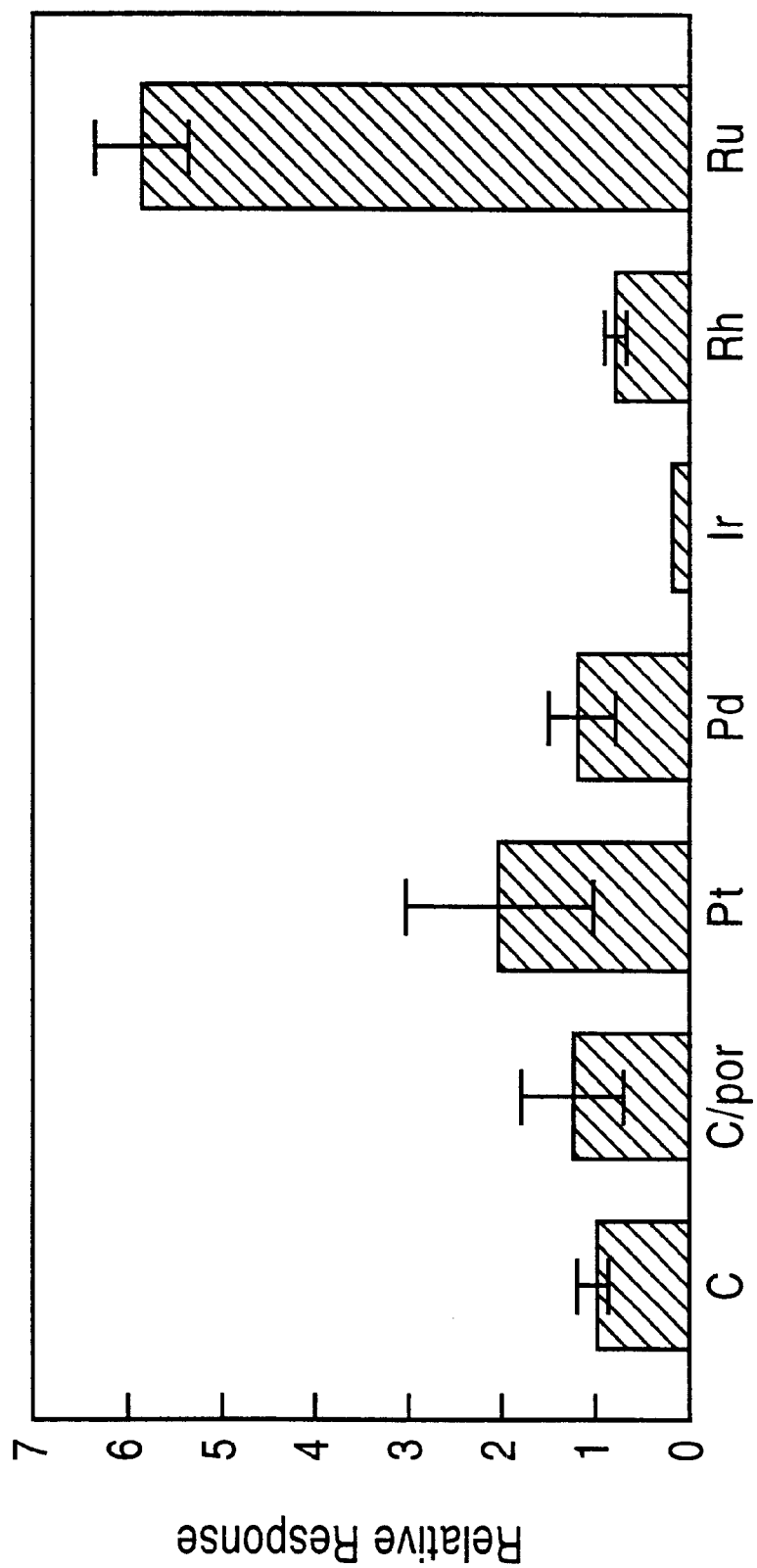
FIG. 1 is a bar graph plot showing the relative responses to nitric oxide of 0.5 mm diameter disk electrodes made of various materials, including an electrode according to the present invention, wherein the response of a carbon electrode is arbitrarily equal to 1, and wherein C=carbon, C/por=carbon coated with a nickel porphyrin, pt=platinum, Pd=palladium, Ir=iridium, Rh=rhodium and Ru=ruthenium.

The electrodes of this invention can be incorporated into a broad variety of biomedical and/or clinical medical devices to facilitate biomedical research and to enable the accurate and/or early diagnosis and monitoring of various medical conditions and/or disease states in which nitric oxide plays a role. For example, the electrodes of this invention may be incorporated into catheters, needles, cannulas and the like for insertion into a patient or experimental subject (e.g., intravenously, into a synovial capsule (joint capsule), into the cerebrospinal fluid, or through a natural body orifice, such as the urethra). The electrode may thus be brought into proximity to a particular biological fluid, such as blood, urine, synovial fluid and the like to allow for the real time detection in vivo of nitric oxide therein. The electrodes of this invention may therefore be employed usefully for the diagnosis and/or monitoring of bacterial infections (e.g., sepsis), autoimmune diseases (e.g., rheumatoid arthritis) and any other disease or condition in which nitric oxide plays a role. Suffice it to say here that the electrodes of this invention may also be incorporated into patient monitoring equipment (e.g., blood drawing systems) or laboratory bench devices.

A greater understanding of this invention will be gained by the following Examples.

EXAMPLE I

Reagents: Phosphate buffered saline (PBS) was prepared by dissolving NaCl (to a final concentration of 150 mM) in 7.0 pH phosphate buffer (Fisher). Nafion™ perfluorinated ion-exchanger resin (5 wt % in lower aliphatic alcohols and water) was purchased from Aldrich Chemical Company and used as supplied. $N_2$ (Ultra High Purity Grade, containing less than 5 micromolar $O_2$) was supplied by National Welders; and 10% NO. in $N_2$ (actual analysis: 9.98% NO., balance $N_2$) was supplied by National Specialty Gases. Nickel(II)-Tetrakis(3-methoxy-4hydroxyphenyl) porphyrin (Ni-TMHPP) was supplied by Midcentury Chemical Co. (Posen, Ill.) and used without further purification.

Instrumentation and Electrodes: The electrochemical responses of test electrodes were observed with a model BAS 100-B potentiostat equipped with a preamplifier, model PA-1, and an electrically-shielded cell stand, model CS-2, all manufactured by Bioanalytical Systems (West Lafayette, Ind.). Data were recorded on a personal computer.

Disk electrodes were fabricated in the laboratory from 1-cm lengths of metal wire or carbon rod. The following precious metals and alloys were supplied by Aldrich Chemical Company: Ir (99.9%), Pd (99.99%), Pt (99.99%), and Rh (99.9%). Centerless ground ruthenium slugs (99.9%) were supplied by Englehard Corp. Carbon rod was improvised from mechanical pencil refills consisting of carbon particles in a polymer binder, as manufactured by Scripto (Ultrapolymer Leads™, HB hardness grade). All electrode materials were 0.5 mm in diameter and in the form of a round solid cylinder, except for the 99.9% Iridium, which is difficult to draw as a round wire (Mohs hardness 6.5). Thus, Iridium was supplied as a solid square cylinder, 0.5 mm on a side.

Electrical leads were prepared by stripping 1 cm of electrical insulation from each end of an 8 cm length of 30 AWG solid copper wire insulated with Kynar™, which withstands temperatures above 300° C. (Radio Shack). Each electrode slug was wrapped tightly with stripped copper wire. The electrode and its electrical lead were then inserted into a 6 cm length of shrink-melt tubing, a tetrafluoroethylene (TFE) tube with a fluorinated ethylene propylene (FEP) lining (Small Parts Co.), with the tip of electrode flush with one end of the tubing and the excess lead wire protruding from the other end. This assembly was heated to approximately 350° C. with a thermostatically-controlled heat gun until the TFE tubing shrunk snugly around the electrode and the FEP lining melted to transparency.

After encapsulation, a disk of the electrode material was exposed by cutting through the melted tubing as close to the metal electrode tip as possible. This exposed disk was polished, first on 600 grit silicon carbide abrasive paper (Buehler) in water, and then successively with aqueous slurries of powered alumina abrasive (Buehler) of 0.5, 0.3, 0.1 and 0.05 $\mu$m particle size. Electrodes were cleaned ultrasonically in de-ionized water after each polishing step. After polishing was completed, each electrode was given a final ultrasonic cleaning in methanol. The integrity of the seal of the FEP liner around the electrode was later tested by observing repeated cyclic voltamograms in potassium ferricyanide solution. The near superposition of repeated voltamograms after 10 cycles was taken to indicate that analyte did not creep by capillarity between the electrode material and its encapsulation, thereby increasing the effective surface area of the electrode. The electrical resistance of the electrode assembly measured less than 0.5 $\Omega$ in all cases, even after immersion in buffered saline solution for two weeks, suggesting that significant corrosion of the encapsulated connection between the copper lead wire and the electrode slug did not occur.

Coating Carbon Electrodes with Porphyrin: Two kinds of carbon electrodes were evaluated for purposes of comparison with the electrodes of this invention—these being, a carbon electrode without a porphyrin coating and a carbon electrode with a metalloporphyrin coating. The porphyrin-coated carbon electrode was prepared by immersing a polished and rinsed carbon electrode in 0.5 mM Nickel(II)-Tetrakis(3-methoxy-4-hydroxyphenyl) porphyrin (Ni-TMHPP) in 0.1M NaOH. Cyclic Voltammetry was performed (-200 to 1200 mV at 100 mV/s) at room temperature (approximately 21 ° C.) for 50 cycles. The deposition of successive layers of the metalloporphyrin could be followed by observing the growth in the Ni(II)/Ni(III) oxidation peaks.

Measuring Effective Areas of Disk Electrodes: After each electrode was polished and rinsed, it was suspended in 10 mM $K_3Fe(CN)_6$ in 1M KCl, along with an Ag—AgCl reference electrode (filled with 3 M KCl) and with a Pt auxiliary electrode. The solution and electrodes were contained in a glass, water-jacketed electrochemical cell maintained at 35°±1° C. Linear Scan Voltammetry was performed (from 400 to 0 mV at 1mV/s). The plateau currents of the resulting sigmoidal current-vs-voltage curves were calculated using an algorithm provided in the BAS software. The effective surface area of each disk electrode was calculated by using the expression:

$$i=4n\ FrDC$$

where:
- i=Steady state current (wave current)
- n=Electrons per molecule oxidized or reduced (n=1 for $Fe(CN)_6^{3-/4-}$)
- F=Faraday's constant
- r=Radius of electrode (cm); Surface Area=$\pi r^2$
- D=Diffusion coefficient (for ferricyanide at 35° C., $cm^2$/sec)
- C=Concentration of ferricyanide ($mol/cm^3$)

Coating Metal and Carbon Electrodes with Nafion™ Resin: Immediately after the effective surface area of each disk electrode was determined as described above, the electrode was dipped and agitated three times in deionized water to rinse off the ferricyanide and KCl solution and then dried in an oven at 80° C. for 10 min. The electrode was then dipped in Nafion™ resin for 10 seconds after which it was again oven dried at 80° C. for 10 min. The initial Nafion™ resin dip followed by drying was repeated 4 times, resulting in a total of 5 coats of Nafion™ resin on each electrode. Completed electrodes were stored overnight in room air in a loosely-covered container. Electrode tips were soaked in PBS for 24 hours prior to use in order to assure complete hydration of the hygroscopic Nafion™ resin membrane.

Preparation of NO. Standard Solutions: Aqueous NO. standards were prepared by saturating PBS with 10% NO. under anaerobic conditions. A glass vial containing 15 mL PBS was sealed with a rubber septum penetrated by small-diameter stainless steel HPLC tubing which extended to near the bottom of the PBS. The septum was also penetrated by a 30 gauge syringe needle to vent the headspace. The PBS was bubbled with humidified $N_2$ for 20 min to lower dissolved oxygen concentration to 5 ppm or less, after which it was bubbled with 10% NO. in $N_2$ for 20 minutes before use; bubbling with 10% NO. was continued throughout each experiment.

Determining Electrode Response to NO.: Each test electrode was immersed in 2.5 mL PBS along with a reference and auxiliary electrode in a water-jacked electrochemical cell maintained at 35°±1° C. as already described; however, the reference electrode was also filled with PBS (instead of 3 M KCl) in order to minimize junction potentials. The analyte buffer was de-aerated by bubbling for 20 minutes with $N_2$ that was humidified by passage through de-ionized water. After the initial de-aeration by bubbling, $N_2$ was kept flowing into the headspace above the buffer.

For an initial two-hour conditioning period, each test electrode was held at a fixed potential of 800 mV with respect to the reference. This potential was chosen because the amperometric response to NO. increased with potential for the materials tested, and when various potentials below 800 mV were tested, there was a decreased response to NO. On the other hand, above 800 mV there was a sharp increase in background current for all electrode materials, presumably due to chloride oxidation or the electrolysis of water (evolving $OH^-$). Therefore, because the electrodes invariably gave the best response at higher potentials, and because 800 mV was as high as one could go without interference from chloride or hydroxyl ions, 800 mV was selected to be the standard potential at which all electrode materials were tested.

All this was done prior to obtaining ruthenium metal for testing, and the behavior of ruthenium was not as expected. Though it gave a poorer response to NO. than other materials at 800 mV, it exhibited an excellent response at a significantly lower potential, contrary to all other materials tested. By later testing ruthenium at a variety of potentials between 0 and 1,000 mV, it was discovered that the oxidation current in the presence of nitric oxide reached a maximum at 675 mV in time-base amperograms. At that potential, ruthenium's response to NO. was better than that of all other materials tested at 675 mV, and even when the other materials were tested at a higher potential, including 800 mV, ruthenium's response at 675 mV was significantly better. It is important to note that for amperometry in complex, biological systems, less extreme potentials (those closer to 0) are to be preferred, because in such systems there is always a mixture of electroactive chemical species, and at higher potentials more of these species may be electrolyzed, producing a current that could be confounded with that due to oxidation of NO.

As described above, all electrodes were maintained at the fixed potential (800 mV, 675 MV, or other chosen potential) for two hours before the exposure to NO., in order to allow the electrode current to decay to a stable baseline. This decay is presumably due partly to charging of the electrode-solution double layer but mostly to the slow formation of an oxide layer.

After the conditioning period, the 800 mV potential for the comparative electrodes, 675 mV for the invention electrode, was maintained without interruption for an additional 4,000 sec (1 hr, 6 min and 40 sec, a maximum imposed by the BAS potentiostat software) while amperommetry was performed as various volumes of the NO. calibration solution were injected into the PBS solution with a Hamilton gas tight syringe (25 $\mu$L, 1700 series). Injections were made at 10-minute intervals, for example, 25, 20, 15, 10, 5, 25, $\mu$L.

Results: The bar graph in the accompanying FIG. 1 shows the results (and standard deviations) obtained when testing the response of various electrode materials to nitric oxide (approximately 0.5 to 1.5 $\mu$M). Each bar represents three or more experimental points. Response is current per unit area of electrode surface per unit concentration NO., expressed relative to the response of a carbon electrode (C). As noted above, all electrodes were held at +800 mV vs Ag/AgCl except the ruthenium electrode, which was held at +675 mV.

As is evident from the bar graph of the accompanying FIG. 1, the electrode according to this invention formed of ruthenium showed considerable improvement over the amperometric response of other electrode materials. It should also be apparent that the ratio of variation in experimental results (standard deviation) to signal strength is best for ruthenium.

Figure 2:
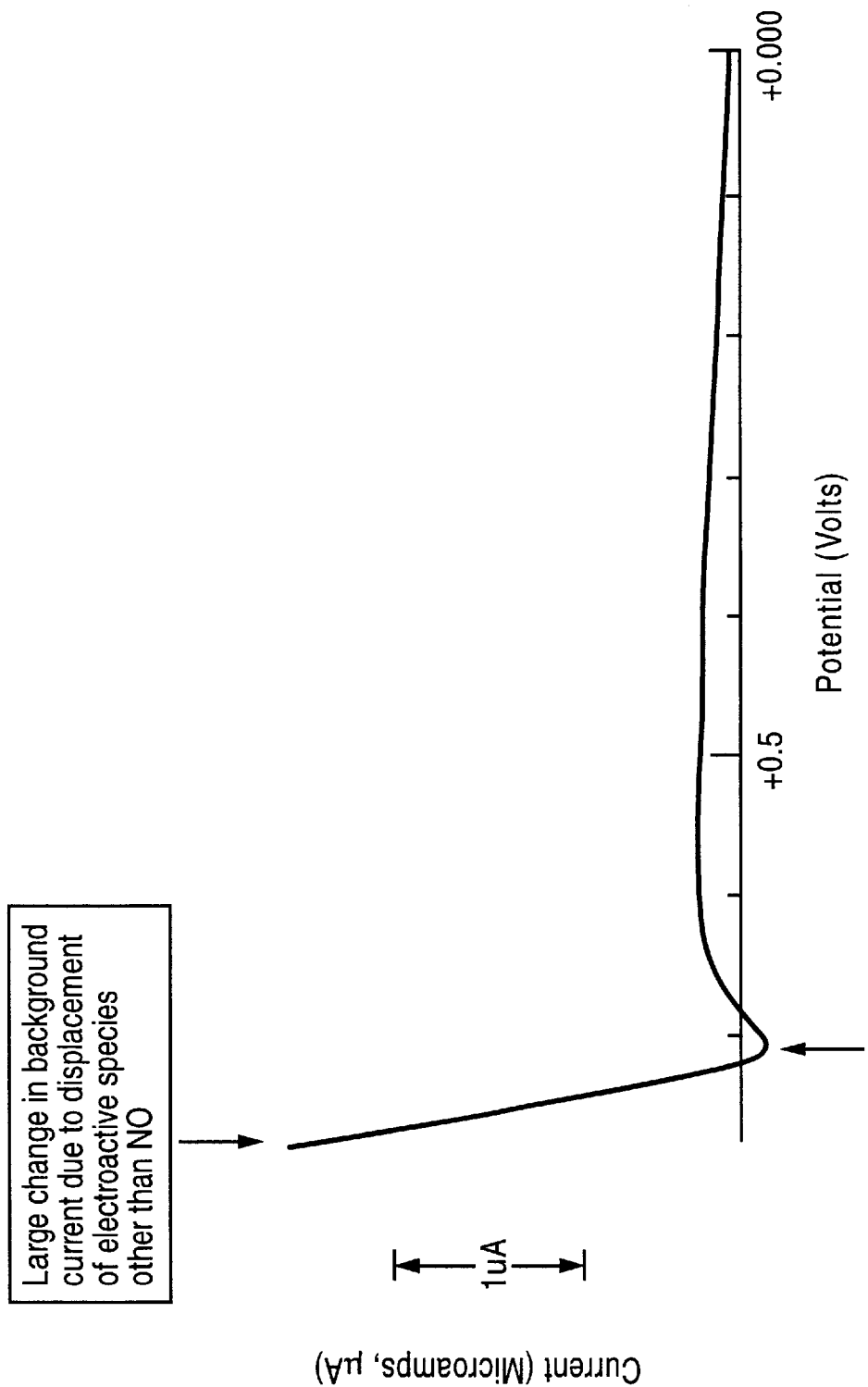
FIG. 2 is a graphical plot of the difference in current between two linear sweep voltamograms using a 0.5 mm ruthenium electrode in the presence and the absence, respectively, of nitric oxide.

Accompanying FIG. 2 exhibits an NO.-induced change in background current that is significantly larger than the current due to direct oxidation or reduction of nitric oxide. Thus, the electrodes of this invention offer the possibility of indirect detection of nitric oxide, since under certain conditions the formation of nitroxyl complexes on the electrode surface may displace other electroactive species (e.g., chloride, Cl$^-$), thereby causing a detectable change in background current.

EXAMPLE II

In order to confirm the conclusion that NO. forms a complex with the Ru-based electrode, two series of experiments were undertaken. In the first series changes were probed in the surface of an electrode prepared from Ru that occur after exposure to a fixed potential and subsequent exposure to NO. These experiments clearly show a change in the capacitance of the electrode after polarizing it at +675 mV for 2 hours. This change is largely reversible on introduction of NO. into the system. In the second series of experiments, the extent to which the oxide film on the Ru electrode can be electrochemically reduced is shown to be severely diminished when surface sites are blocked by adsorbed NO. Taken together, the data from both series of experiments lend strong support to the mechanism herein proposed for the enhanced sensitivity of the Ru electrode towards oxidation of NO., i.e. surface complexation.

When a metal electrode (e.g., Ru) is immersed in an electrolyte solution, ions in solution adsorb at the electrode/solution interface to counterbalance any excess electronic charge on the metal, forming a double layer. Under ideal conditions, the double layer behaves like a simple capacitor, charging and discharging as the potential difference between the metal electrode (e.g. Ru) and the reference electrode (e.g. Ag/AgCl) is changed. The amount of charge (Q) that can be stored on a capacitor held at a potential (E) depends on the system capacitance (C) according to:

$$Q = E \times C$$

However, when a molecule (e.g., NO.) adsorbs onto the surface of the metal electrode, the capacitance of the double layer must change. This is analogous to changing the dielectric constant of the material between the plates of a simple parallel-plate capacitor. The capacitance (C) is first-order with respect to the dielectric constant (e) of the medium between the plates as given by:

$$C = (e \times e_0)/d$$

where ($e_0$) is the permittivity of vacuum, and d is the spacing between the plates of the capacitor. Thus, measuring the capacitance of an electrode in an electrolyte before and after exposure to an analyte molecule (e.g., NO.) can be used to determine if the molecule adsorbs on the electrode. Measurable changes in capacitance are expected when the analyte adsorbs strongly on the electrode.

When a potential pulse is applied to an electrode, a current response will arise due to charging or discharging of the double layer. At short times (tens of milliseconds or less) the total current measured will be comprised exclusively of this charging current. Charging current ($i_c$) is given by the expression:

$$i_c = (\Delta E/R) \times exp(-t/RC)$$

where $\Delta E$ is the magnitude of the potential pulse applied (in Volts), R is the solution resistance (in ohms), t is time (in sec), and C is the double layer capacitance (in Farads). Thus, double layer capacitance is determined by plotting the logarithm (In) of charging current versus time according to:

$$ln(i_c) = ln(\Delta E/R) - (t/RC)$$

Since $\Delta E$ is known (experimentally specified in this case), the y-intercept from the above procedure gives the solution resistance, and the double layer capacitance can be obtained from the slope of the plot. The instrumentation used in these experiments (a BAS 100B potentiostat) actually implements the above experiment in the following way. A symmetrical, square wave voltage pulse, centered about a user-selected dc-offset potential (dc ±25 mV), is applied. Two current samples are then taken; one at 54 microseconds ($\mu s$) after imposition of the potential pulse and another at 72 $\mu s$ after the pulse. The value of the solution resistance is then obtained by extrapolation to t=0 of the best-fit line through the two values for current. This procedure (imposition of a pulse, taking of two current measurements, and extrapolation to t=0) is automatically repeated 256 times, and a mean value for R is obtained. A mean time constant (RC) is also obtained, defined as the time needed for the current to decay to 37% of its initial, instantaneous value.

First experimental series. This set of experiments was conducted to determine if the capacitance of an oxide-covered Ru electrode is altered by exposure to NO. (The oxide film in these experiments was grown by holding the electrode at a potential of 675 mV for 2 hours, but could presumably be generated by chemical oxidation, instead.) In these experiments: (1) A 500 $\mu m$-diameter Ru electrode was polished, and its capacitance (C) measured at a variety of dc-offset potentials. (2) The electrode potential was then held at ±675 mV vs. the Ag/AgCl reference for 2 hours (the so-called "Quiet Time" or QT). The electrode capacitance was then re-measured. (3) The experiment was repeated, this time exposing the electrode after the QT to 10% NO. ( by maintaining 10% NO. in the headspace above the analyte solution), measuring the capacitance again at each dc-offset potential, and calculating the mean value of C. (4) Finally, the experiment was conducted once again, this time exposing the electrode to 10% NO. for 30 minutes after the QT and then purging with $N_2$ for 30 minutes, and the mean value of C was then determined as before.

The table below summarizes these data and includes control data for a Pt electrode. Specifically, the data below are initial and final values for mean capacitance in micro-Farads ($\mu F$) of 500 $\mu m$ diameter Ru and Pt electrodes, with the values shown in parentheses being the percent (%) difference between initial and final capacitance measurements.

|  | After Polishing | After Quiet Time (QT) | After QT + NO· | After QT + NO· + $N_2$ |
|---|---|---|---|---|
| Ruthenium: | 0.290 $\mu F$ | 0.589 $\mu F$ (+103%) |  |  |
|  | 0.326 $\mu F$ |  | 0.378 $\mu F$ (+16%) |  |
|  | 0.419 $\mu F$ |  |  | 0.815 $\mu F$ (+95%) |
| Platnium: | 0.252 $\mu F$ | 0.252 $\mu F$ (0%) |  |  |

As is evident from these data, a measurable and significant increase in capacitance occurs in the Ru electrode after the QT, but not in the Pt electrode. Also, the reversible decrease in capacitance of the Ru electrode that occurs after exposure to NO. is evident.

Several conclusions may be drawn from the first experimental series: (1) Polarizing a Ru electrode at ±675 mV for 2 hours results in a significant increase in the measured capacitance which could, in principle, be caused either by formation of an oxide film on the surface or by potentiostatic surface roughening, which could increase the microscopic surface area of the electrode. The former explanation is favored, as discussed below. (2) On the other hand, polarizing a Pt electrode at +800 mV (the potential most likely to show an effect on Pt) for 2 hours does not appear to affect the measured electrode capacitance. (3) Exposure to 10% NO. of an Ru electrode which has previously been held ±675 mV for 2 hours causes the measured electrode capacitance to return to a value nearly equal to that for a freshly polished electrode. This strongly suggests that the 2-hour quiet time (polarization at ±675 mV) causes formation of an oxide layer rather than a change in surface roughness (i.e. a change in microscopic area). That is, there is no reason to expect that exposure of roughened Ru to NO. would smooth the surface. (4) The fact that the capacitance of the oxide-covered Ru electrode decreases after exposure to NO. provides evidence of a specific chemical interaction between NO. and the electrode surface. This interaction is apparently reversible, since the adsorbed NO. can be displaced by $N_2$. That is, nitrogen saturation of a solution into which the NO.-treated Ru electrode is immersed results in restoration of the capacitance value that had previously been observed after 2-hours of polarization (QT). (5) The results of this first series of experiments, when taken together, provide strong electrochemical evidence for the existence of a surface complex (or complexes) forming between NO. in a saline medium and an Ru electrode, but not with a Pt electrode. Apparently, this complexation only occurs if the surface of the Ru electrode has previously been partially oxidized.

Second experimental series. This set of experiments was conducted to determine if the presence of NO. affects the oxide film grown on the surface of the Ru electrode during the QT.

The formation and destruction of oxide films on electrode surfaces can also be probed directly using the electrochemical technique called cyclic voltammetry. In this technique, the voltage of the Ru electrode relative to a reference electrode (Ag/AgCl in this case) is caused to change and the resulting current is monitored. Forcing the voltage to a positive value drives formation of the oxide layer, and an anodic (oxidation) current is registered. Conversely, when a negative voltage is applied, the oxide film is reduced to regenerate the "bare" Ru metal, and a cathodic (reduction) current is observed. As will be shown below, the interaction of NO. with the surface of an Ru electrode prevents reduction of the oxide layer. This is indicative of the formation of an inner coordination sphere complex between NO. and the Ru surface, thus shifting the reduction potential of the Ru—O functional groups on the surface.

Figure 3:
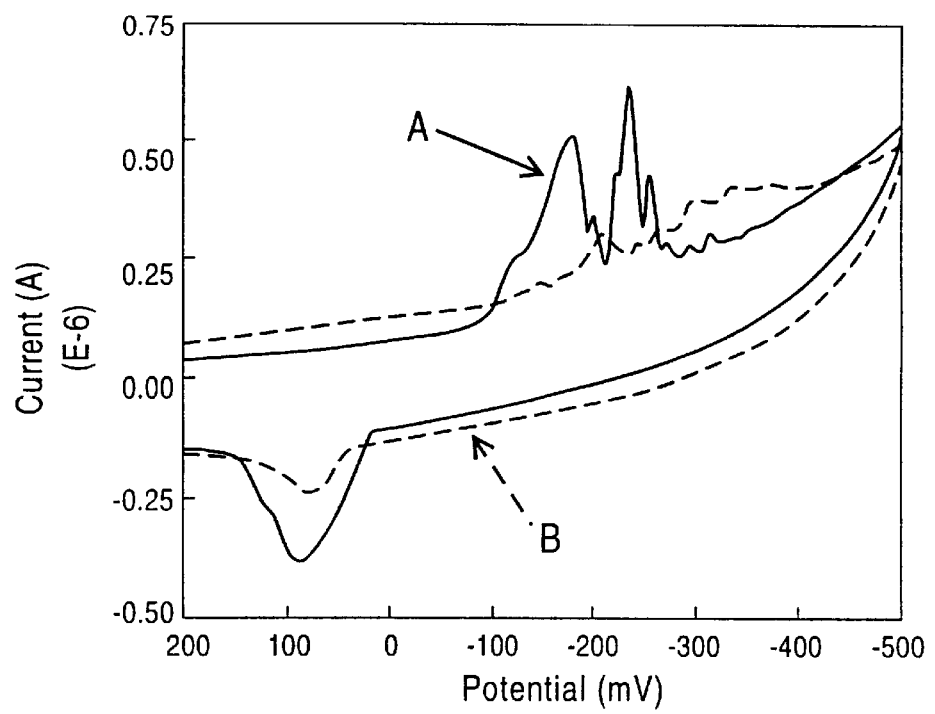
FIG. 3 is a graphical plot which shows the results of the cyclic voltammetric results of the second series of experiments described below in Example II.

Voltammogram (A) of accompanying FIG. 3 was obtained at an Ru electrode immersed in nitrogen-saturated phosphate buffered saline (PBS). The upward-going peaks appearing at about −175 and −245 mV are due to the reduction to elemental Ru of various oxides (Ru—$O_x$, where x is a positive number greater than 0, for example, between 0 up to and including 2 and greater.). Voltammogram (B) of accompanying FIG. 3 was obtained after saturation of the saline solution with 10% NO. and shows that reduction of Ru is greatly inhibited in the presence of NO.

The voltammograms in FIG. 3 show clear interactions between NO. and the oxide layer on a Ru electrode. The upward-going peaks that appear at about −175 and −245 mV are due to the reduction to elemental Ru of various Ru oxides. As can clearly be seen, these upward-going (reduction) peaks in the voltammogram A obtained using an Ru electrode immersed in nitrogen-saturated PBS have largely disappeared in voltammogram B obtained using the Ru electrode in PBS saturated with 10% NO., and the greatly-diminished remnants of those peaks have shifted to more negative potentials. This indicates a chemical change in the Ru—$O_x$ layer due to the presence of NO. For example, formation of an adlayer of Ru—O—NO or Ru(Cl$_x$)—O—NO having a more negative reduction potential than the original Ru—O$_x$ would be consistent with these results.

The conclusion reached from this second series of experiments, together with the capacitance data from the first experimental series, is that partial oxidation of an Ru electrode in aqueous saline creates a surface onto which NO. can adsorb and be easily detected by electrochemical means. Our previous data have shown that polarization of the electrode at +675 mV is optimal for formation of the useful oxide layer. Use of more positive potentials results in a drastically diminished sensitivity. Furthermore, published Pourbaix diagrams for Ru (that is, diagrams of potential vs. pH; see J. F. Llopis et al, "Ruthenium," chapter VI-8, A. J. Bard, Encyclopedia of Electrochemistry of the Elements, Marcel Dekker, Inc. (1976), the entire content of which is expressly incorporated hereinto by reference) lead us to suspect that the active oxide is not RuO$_2$, but must consist of a continuously-variable mixture of elemental ruthenium and its oxides RuO$_x$, where x is a positive number from just above 0 through higher oxidation states, even above 2, and includes fractional values.

EXAMPLE III

Figure 4:
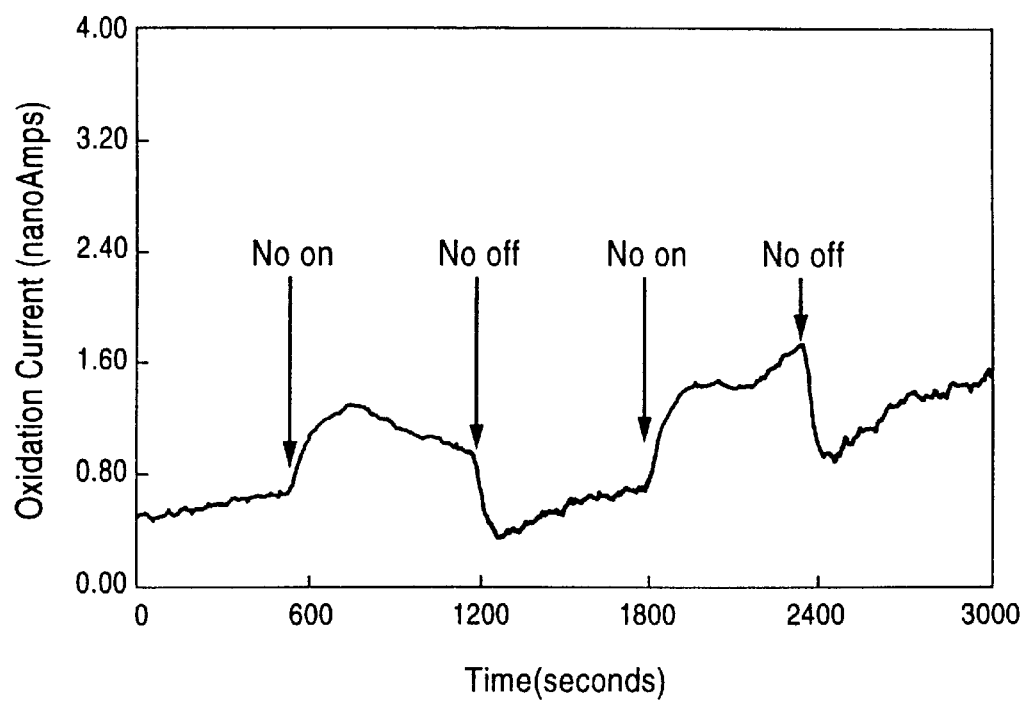
FIG. 4 is a graphical plot showing the detection of 1.5 μM nitric oxide added to human blood plasma.

In order to demonstrate electrode efficacy in a complex biological fluid containing proteins, a ruthenium working electrode, an Ag/AgCl reference electrode, and a Pt auxiliary electrode were employed in an electrochemical cell containing a 2 ml stirred sample of human blood plasma to which 1.5 $\mu$M nitric oxide was added. The gas flowing continuously in the headspace above the stirred sample was 100% N$_2$ which was periodically alternated with 0.1% NO. in N$_2$. The original blood sample was collected in a Vacutainer™ sample container (Becton Dickinson & Co.) in Li-heparin. As is evident from the plot of accompanying FIG. 4, the electrode of this invention accurately detected the presence of nitric oxide in the sample.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrode having a surface region comprised of a metal oxide capable of enhanced detection of nitric oxide when exposed to a nitric oxide-containing fluid.

2. The electrode of claim 1, wherein at least the surface region comprised of at least one oxide of ruthenium.

3. The electrode of claim 1, wherein said at least one surface region is comprised of at least one oxide of ruthenium having the formula RuO$_x$, where x is a number greater than 0.

4. The electrode of claim 3, wherein x is a number greater than 0 up to and including about 2.

5. The electrode of claim 1, wherein at least the surface region consists essentially of ruthenium conditioned at a potential for a time sufficient to cause the surface region to exhibit maximal nitric oxide response when exposed to the nitric oxide-containing fluid.

6. A nitric-oxide specific electrode having a surface region conditioned at a potential which enhances nitric oxide detection when the electrode is exposed to a nitric oxide-containing fluid.

7. The electrode of claim 6, wherein said at least one oxide of ruthenium is RuO$_x$, where x is a number greater than 0.

8. The electrode of claim 7, wherein where x is greater than 0 up to and including about 2.

9. A medical device which comprises an electrode according to any one of claims 1–8.

10. The device of claim 9, adapted to detect nitric oxide in a biological fluid.

11. The device of claim 10, wherein the biological fluid is at least one of blood, urine and synovial fluid.

12. A medical device as in claim 9 adapted for the in vivo detection of nitric oxide in a biological fluid.

13. A method for the in vivo detection of nitric oxide comprising placing an electrode according to any one of claims 1–8 at a site within a patient or other living organism, and then determining the nitric oxide present at said site by the electrochemical response of said electrode.

14. A method of detecting nitric oxide in a biological sample comprising bringing an electrode according to any one of claims 1–8 into contact with the biological sample, and then determining the nitric oxide present in said sample by the electrochemical response of said electrode.

15. A method of making an electrode for the detection of nitric oxide which comprises conditioning a metal electrode surface at a potential for a time sufficient for the surface to exhibit enhanced nitric oxide response.

16. The method as in claim 15, wherein the metal electrode surface is held at a potential for a time sufficient to allow electrode current to decay to a stable baseline.

17. An electrode for the detection of nitric oxide made according to claim 15 or 16.

* * * * *